(12) United States Patent
Barnes et al.

(10) Patent No.: US 8,470,036 B2
(45) Date of Patent: Jun. 25, 2013

(54) METHOD AND APPARATUS FOR RECONSTRUCTING A LIGAMENT

(76) Inventors: William S. Barnes, Forsyth, GA (US); George W. Stough, Alpharetta, GA (US); Christopher C. Bidwell, Dunwoody, GA (US)

( * ) Notice: Subject to any disclaimer, the term of this patent is extended or adjusted under 35 U.S.C. 154(b) by 419 days.

(21) Appl. No.: 12/571,016

(22) Filed: Sep. 30, 2009

(65) Prior Publication Data

US 2010/0100182 A1 Apr. 22, 2010

Related U.S. Application Data

(60) Provisional application No. 61/194,727, filed on Sep. 30, 2008.

(51) Int. Cl.
*A61F 2/08* (2006.01)
(52) U.S. Cl.
USPC .......................................... 623/13.11
(58) Field of Classification Search
USPC ........................................ 623/13.11–13.14
See application file for complete search history.

(56) References Cited

U.S. PATENT DOCUMENTS

| | | | | |
|---|---|---|---|---|
| 6,200,347 | B1 * | 3/2001 | Anderson et al. | 623/16.11 |
| 6,887,271 | B2 * | 5/2005 | Justin et al. | 623/13.14 |
| 6,893,462 | B2 * | 5/2005 | Buskirk et al. | 623/13.17 |
| 7,008,451 | B2 * | 3/2006 | Justin et al. | 623/13.14 |
| 7,513,910 | B2 * | 4/2009 | Buskirk et al. | 623/13.17 |
| 7,727,278 | B2 * | 6/2010 | Olsen et al. | 623/13.12 |
| 7,763,072 | B2 * | 7/2010 | Bianchi et al. | 623/13.14 |
| 2003/0097179 | A1 * | 5/2003 | Carter et al. | 623/13.17 |
| 2005/0159812 | A1 * | 7/2005 | Dinger et al. | 623/13.14 |
| 2007/0225805 | A1 * | 9/2007 | Schmieding | 623/13.14 |
| 2009/0054982 | A1 * | 2/2009 | Cimino | 623/13.19 |
| 2010/0222792 | A1 * | 9/2010 | Barnes et al. | 606/148 |

* cited by examiner

*Primary Examiner* — Suzette J Gherbi

(57) ABSTRACT

Apparatus for use in supporting a graft ligament within a bone tunnel, the apparatus comprising a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith; wherein the graft ligament plug is formed in two opposing halves, such that the graft ligament can be positioned within the groove and thereafter clamped between the opposing two halves of the graft ligament plug when the two opposing halves are brought together so as to form the complete graft ligament plug.

20 Claims, 13 Drawing Sheets

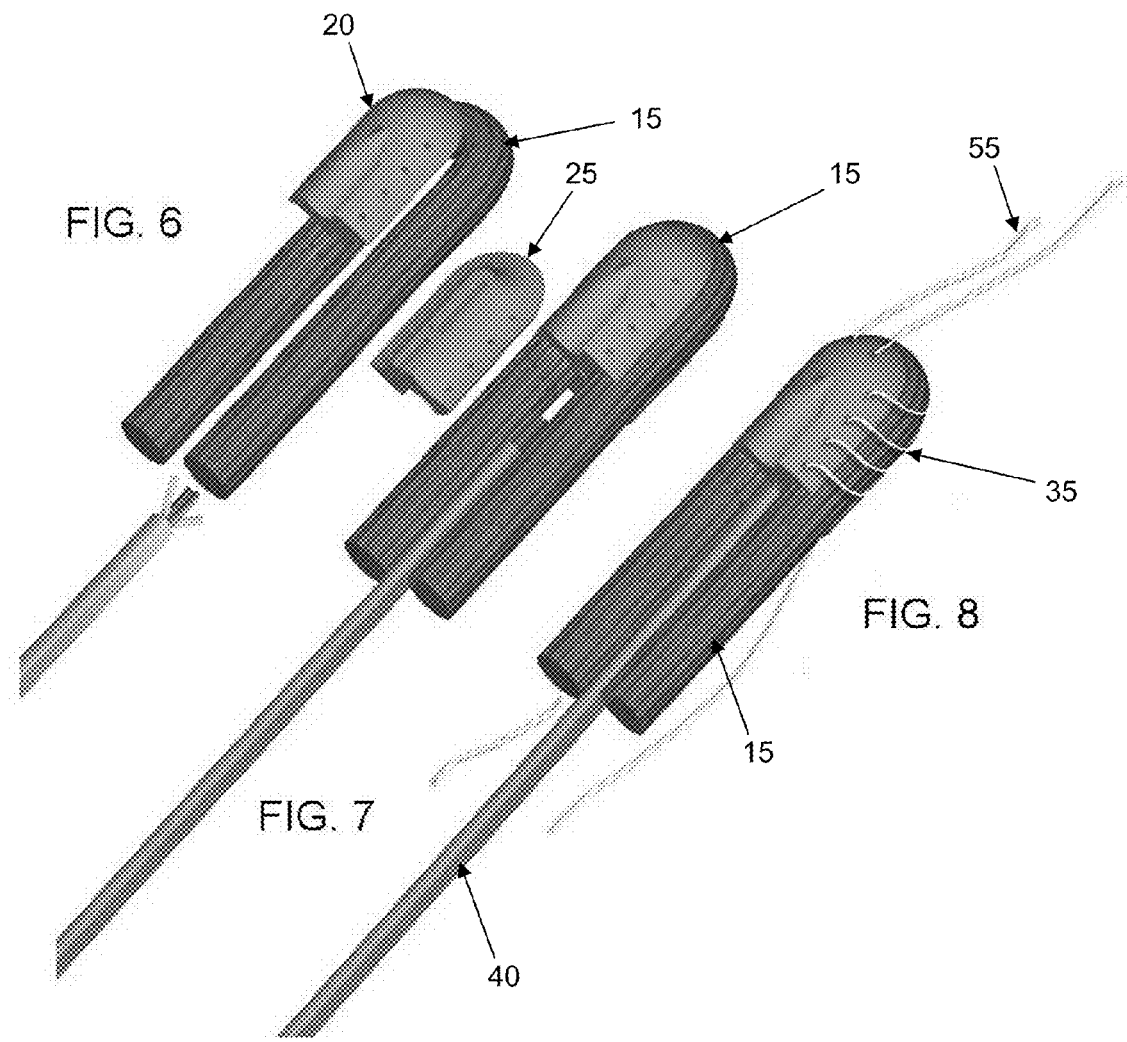

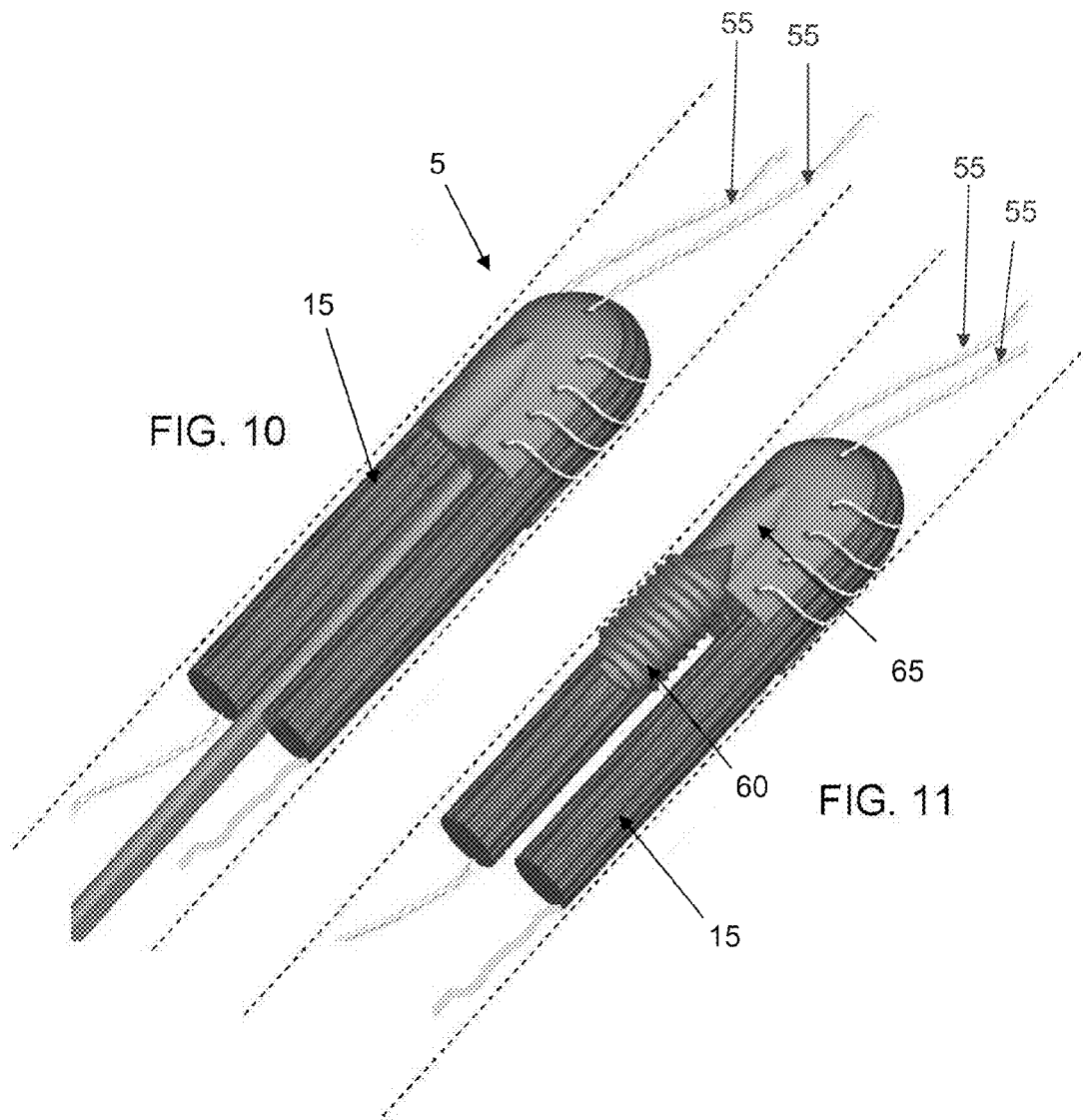

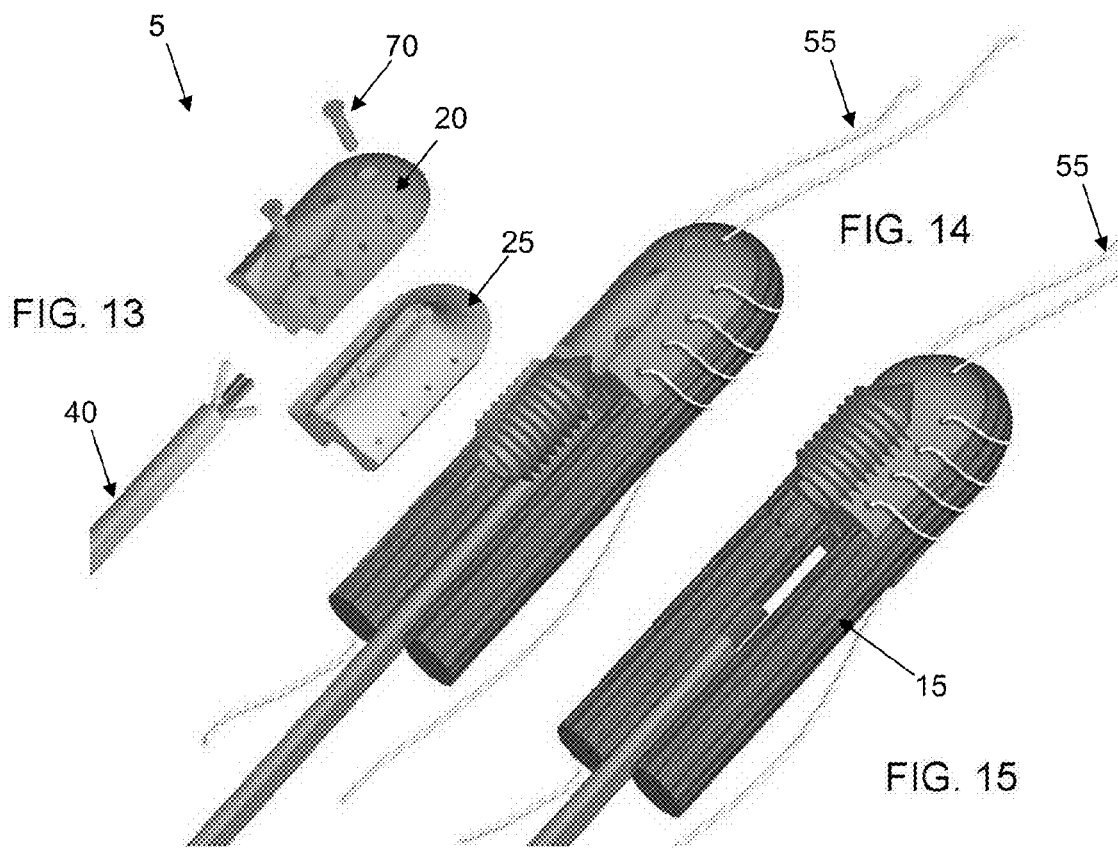

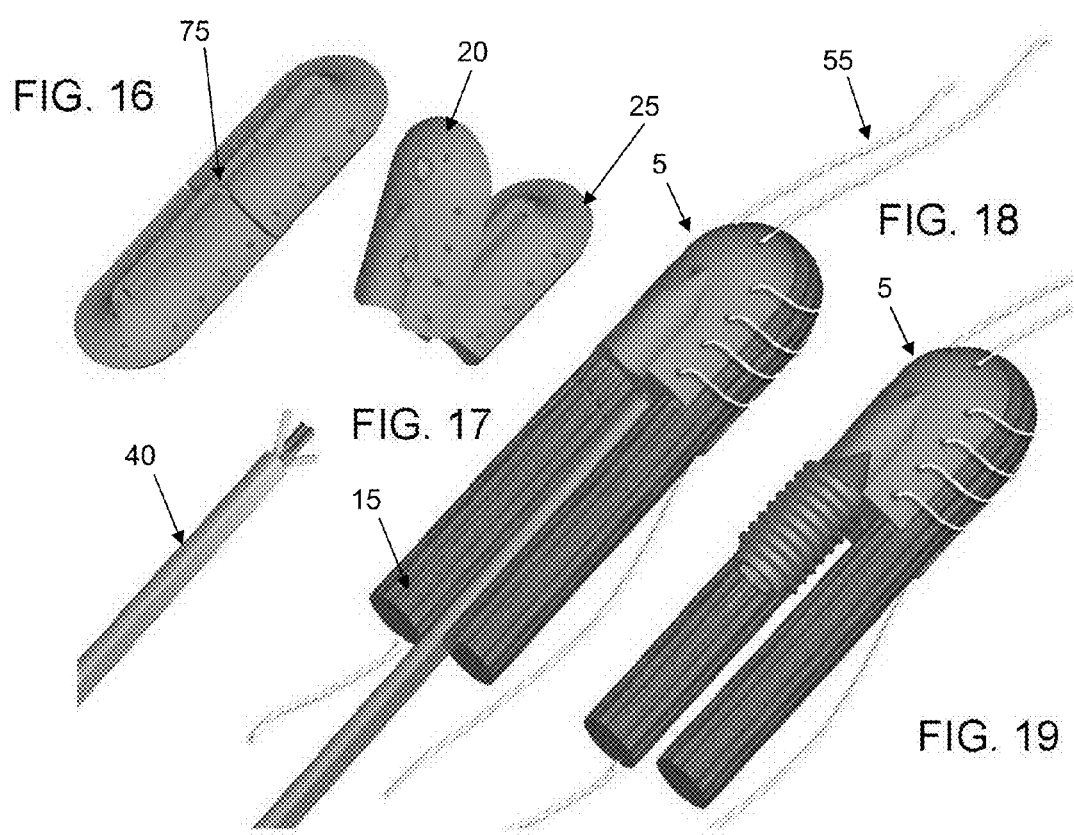

METHOD AND APPARATUS FOR RECONSTRUCTING A LIGAMENT

REFERENCE TO PENDING PRIOR PATENT APPLICATION

This patent application claims benefit of pending prior U.S. Provisional patent application Ser. No. 61/194,727, filed Sep. 30, 2008 by William S. Barnes et al. for METHOD AND APPARATUS FOR RECONSTRUCTING A LIGAMENT, which patent application is hereby incorporated herein by reference.

FIELD OF THE INVENTION

This invention relates to surgical methods and apparatus in general, and more particularly to methods and apparatus for reconstructing a ligament.

BACKGROUND OF THE INVENTION

A ligament is a piece of fibrous tissue which connects one bone to another, e.g., at a joint. Ligaments are frequently damaged (e.g., detached, torn, ruptured, etc.) as the result of injury and/or accident. A damaged ligament can impede proper motion of a joint and cause pain to the patient.

Various procedures have been developed to repair or replace a damaged ligament. The specific procedures used depend on the particular ligament which is to be restored and the nature and extent of the damage to the ligament.

The anterior cruciate ligament (ACL) of the knee is one ligament which is frequently damaged as the result of injury and/or accident. More particularly, and looking now at FIGS. 1 and 2, an ACL is shown extending across the interior of the knee, between the top of the tibia and the bottom of the femur. A damaged ACL can cause instability of the knee, may lead to arthritis and/or damage to other bodily structures, and can cause substantial pain for the patient.

Numerous procedures have been developed to replace a badly damaged ACL through a ligament replacement procedure. More particularly, and looking now at FIG. 3, these ACL replacement procedures generally involve drilling a bone tunnel across the tibia and up into the lower portion of the femur. Then a graft ligament, consisting of a harvested ligament or tendon or an artificial ligament, is passed through the tibial portion of the bone tunnel, across the interior of the joint, and up into the femoral portion of the bone tunnel. Then a distal portion of the graft ligament is secured in the femoral tunnel and a proximal portion of the graft ligament is secured in the tibial tunnel. Over time, the graft ligament osseointegrates with the host bones, providing an effective ligament restoration.

There are currently a variety of approaches to secure the graft ligament within the bone tunnel. These approaches typically depend on (i) whether the graft ligament is being fixed in the femoral tunnel or the tibial tunnel, and (ii) the type of graft ligament which is being used for the ligament replacement procedure.

More particularly, when the graft ligament is to be fixed in the femoral tunnel, the surgical apparatus must generally access the femoral tunnel from the base of the femur, and when the graft ligament is to be fixed in the tibial tunnel, the surgical apparatus must generally access the tibial tunnel from the front of the tibia. As a result, it is common for different types of surgical apparatus to be used, depending on whether the graft ligament is being secured in the femoral tunnel or in the tibial tunnel.

In addition to the foregoing, some ligament reconstruction procedures utilize a graft ligament which is harvested so as to include a portion of a bone block, e.g., a patellar tendon including a portion of the patella. Other ligament reconstruction procedures utilize a graft ligament which is harvested so as to consist entirely of soft tissue, e.g., a harvested hamstring tendon. In general, different types of surgical apparatus are used to secure the graft ligament in the bone tunnel, depending on whether the graft ligament includes a portion of a bone block or is composed entirely of soft tissue.

In practice, it is generally preferable to harvest graft ligaments consisting entirely of soft tissue, e.g., a hamstring tendon, since this is significantly less painful for the patient and reduces trauma to the harvest site. However, graft ligaments consisting entirely of soft tissue are generally more difficult to secure to the host bone, since the soft tissue is generally fairly soft and relatively slippery. In addition, the soft tissue tends to be biologically fragile, requiring greater care to ensure successful osseointegration.

SUMMARY OF THE INVENTION

The present invention provides a new method and apparatus for reconstructing a ligament. More particularly, the present invention provides a new method and apparatus for securing a graft ligament in a bone tunnel.

Significantly, the present invention may be used in an ACL reconstruction where the graft ligament is to be secured in the femoral tunnel, and where the graft ligament is formed entirely out of soft tissue (e.g., where the graft ligament comprises a harvested hamstring tendon).

The present invention may also be used in other types of ligament reconstructions, e.g., to reconstruct other ligaments of the knee, and/or to reconstruct ligaments in other joints, and/or to reconstruct other ligaments in the body.

More particularly, the present invention comprises the provision and use of a novel graft ligament plug for use in supporting a graft ligament within a bone tunnel. The plug is provided with a groove that runs up one side of the plug, across the front end of the plug, and then back down the opposing side of the plug, with the groove acting as a seat for the graft ligament. The plug is formed in two halves so that the graft ligament can be positioned within the groove and then clamped therein, between the opposing halves. Preferably, the groove has a depth such that a portion of the graft ligament protrudes out of the groove, in order that the graft ligament can engage the side and end walls of the bone tunnel to facilitate osseointegration.

The plug, with the graft ligament secured thereto, can be advanced up into the bone tunnel and secured in position so as to support the graft ligament within the bone tunnel. Significantly, the plug can be secured in the bone tunnel in a variety of ways well known in the art, e.g., with an interference screw, a crosspin, a suspension suture, etc.

In one preferred form of the invention, there is provided apparatus for use in supporting a graft ligament within a bone tunnel, the apparatus comprising:

a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;

wherein the graft ligament plug is formed in two opposing halves, such that the graft ligament can be positioned within the groove and thereafter clamped between the opposing two halves of the graft ligament plug when the two opposing halves are brought together so as to form the complete graft ligament plug.

In another preferred form of the invention, there is provided a method for supporting a graft ligament within a bone tunnel, the method comprising:

providing a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;

wherein the graft ligament plug is formed in two opposing halves, such that the graft ligament can be positioned within the groove and thereafter clamped between the opposing two halves when the halves are brought together so as to form the complete graft ligament plug;

mounting a graft ligament to the graft ligament plug so that the graft ligament protrudes from the groove of the graft ligament plug;

positioning the graft ligament plug and the graft ligament within the bone tunnel; and supporting the graft ligament plug within the bone tunnel.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 6-9 are schematic views showing how a graft ligament may be secured to the plug of FIGS. 4 and 5;

FIGS. 10-12 are schematic views showing how the plug of FIGS. 4 and 5 may be used to support a graft ligament within a bone tunnel, and how the plug may be secured to the host bone with an interference screw;

FIGS. 13-15 are schematic views showing another plug formed in accordance with the present invention;

FIGS. 16-19 are schematic views showing still another plug formed in accordance with the present invention;

DETAILED DESCRIPTION OF THE PREFERRED EMBODIMENTS

Figure 1:
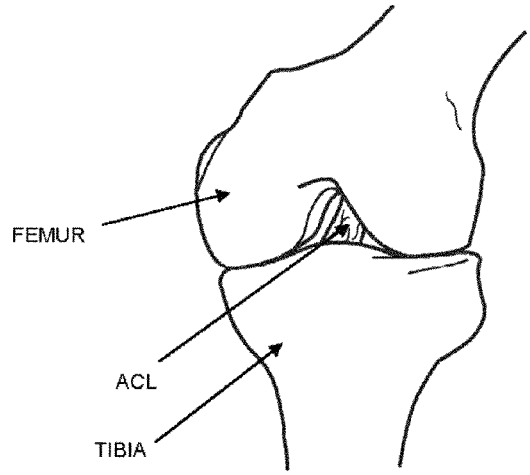
FIGS. 1 and 2 are schematic views of a knee joint, showing an ACL extending between the tibia and the femur.
Figure 2:
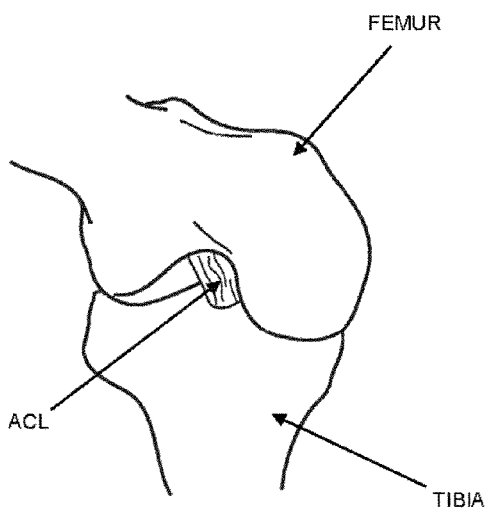
Figure 3:
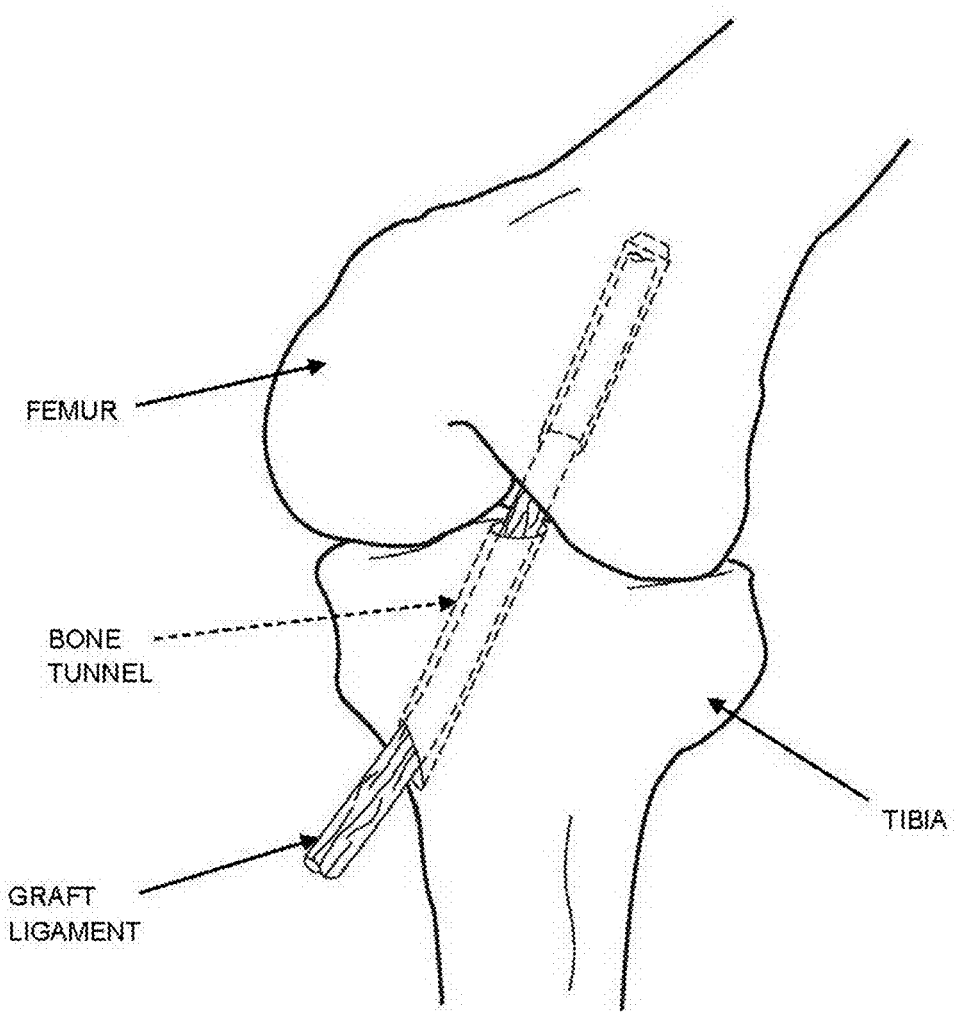
FIG. 3 is a schematic view of a knee joint, showing a graft ligament extending between the tibia and the femur.
Figure 4:
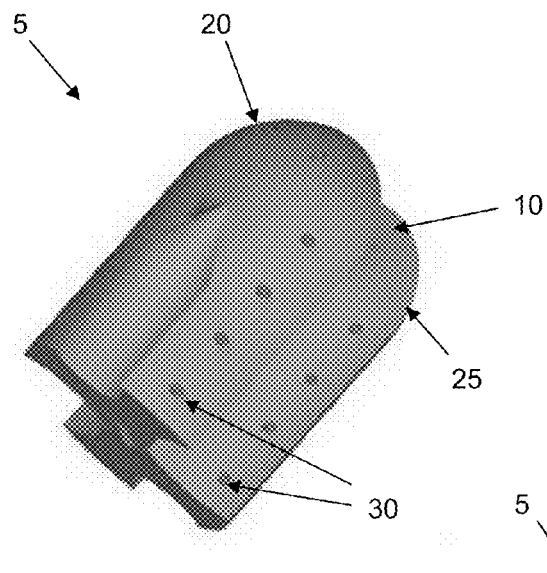
FIGS. 4 and 5 are schematic views showing a plug formed in accordance with the present invention.
Figure 5:
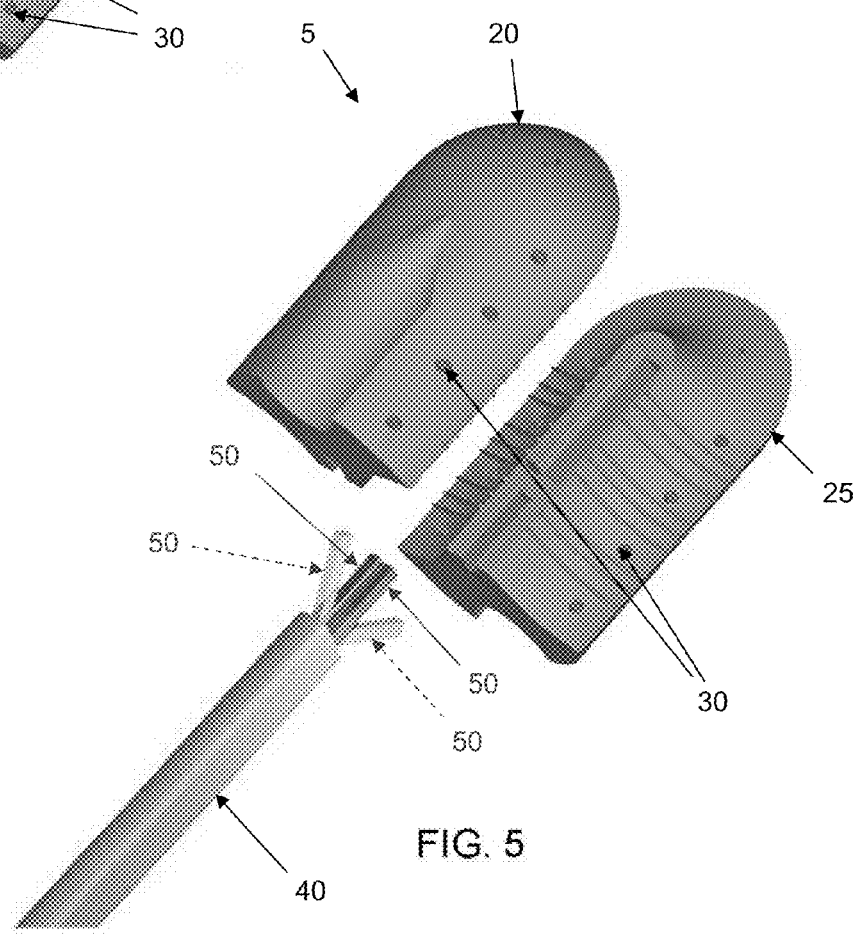
Figure 9:
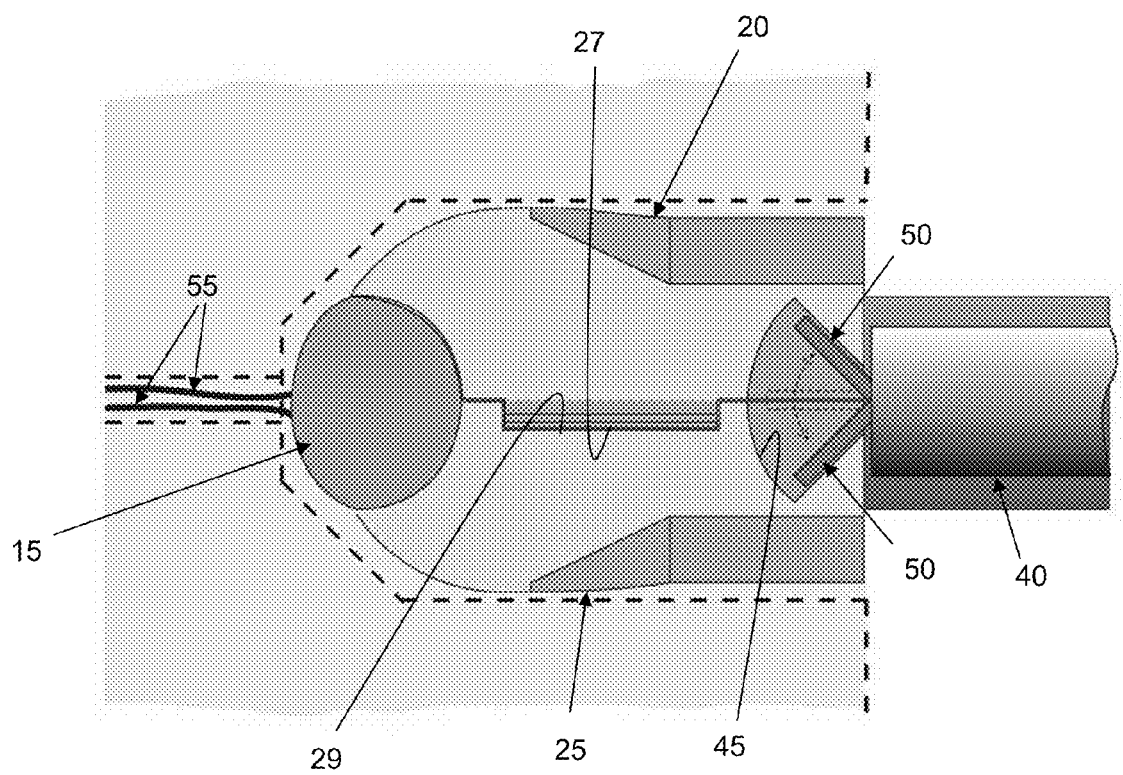

The present invention provides a new method and apparatus for reconstructing a ligament. For convenience, the present invention will hereinafter be discussed in the context of its use for ACL femoral fixation; however, it should be appreciated that the present invention may also be used for other ligament reconstructions within the knee and/or other ligament reconstructions within the body.

Looking now at FIGS. 4-9, there is shown a graft ligament plug 5 formed in accordance with the present invention. As will hereinafter be discussed in further detail, plug 5 may be used to support a graft ligament within a bone tunnel. Plug 5 generally comprises a groove 10 which runs up one side of the plug, across the front (i.e., the distal end) of the plug, and then back down the other side of the plug, with the groove acting as a seat for the graft ligament 15 (FIGS. 6-8). Preferably, groove 10 has a depth such that a portion of graft ligament 15 protrudes out of the groove, in order that the graft ligament can engage the side and end walls of the bone tunnel to facilitate osseointegration.

Plug 5 is formed by two opposing halves 20, 25 so that the graft ligament can be positioned within the groove and then clamped therein, between the opposing halves. To this end, first half 20 and second half 25 may be provided with complementary surfaces 27, 29 (FIG. 9) for mating and locking under controlled compression (ratcheting) with one another when the two halves are brought together. In one preferred form of the invention, complementary surfaces 27, 29 mate and lock with a ratcheting action so as to provide a well-controlled compression. Furthermore, suture holes 30 are provided in first half 20 and second half 25 so that the two halves may be secured together with one or more sutures 35 (FIG. 8), with suture 35 helping to hold graft ligament 15 in groove 10.

Plug 5 (and its associated graft ligament 15) may be advanced into the bone tunnel using an inserter 40 which is releasably mounted to the proximal end of plug 5. To this end, plug 5 may comprise a recess 45 (FIG. 9) which can receive articulating fingers 50 of inserter 40, whereby inserter 40 may be releasably mounted to the proximal end of plug 5. More particularly, when inserter 40 is to be secured to plug 5, articulating fingers 50 of inserter 40 are positioned in a parallel disposition (FIG. 5), the inserter is maneuvered so that fingers 50 extend into recess 45, and then fingers 50 are spread apart (FIG. 9), thereby gripping plug 5 to inserter 40. Significantly, inserter 40 mates with plug 5 with a known relationship (i.e., with a known longitudinal positioning and with a known angular orientation), such that by observing the position and orientation of the handle of the inserter, the surgeon will know the position and orientation of the plug-graft assembly. This construction provides the surgeon with an excellent means to precisely locate the plug-graft assembly within the femoral tunnel while controlling rotation and depth. Correspondingly, when plug 5 is to be released from inserter 40, fingers 50 are positioned in their parallel disposition, and inserter 40 is withdrawn from plug 5.

Additionally, and/or alternatively, plug 5 (and its associated graft ligament 15) may be towed up into a bone tunnel using tow sutures 55 (FIG. 8).

Figure 12:
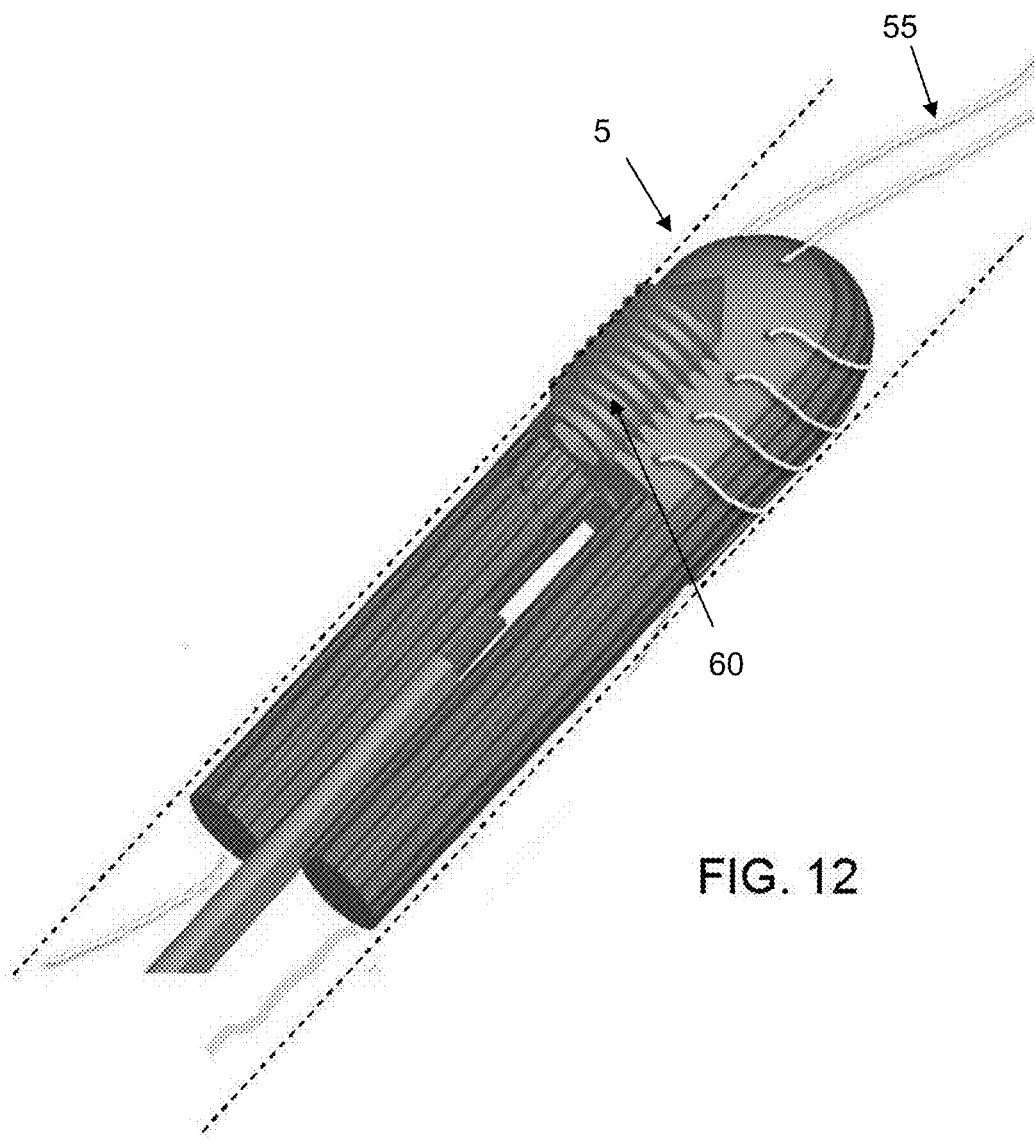
Figure 20:
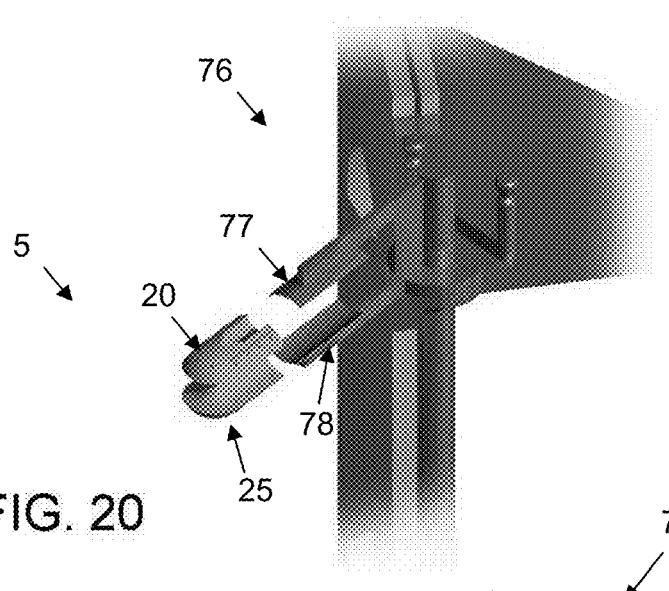
FIGS. 20-23 are schematic views showing a fixture which can be used to support the plug while a graft ligament is secured thereto.
Figure 21:
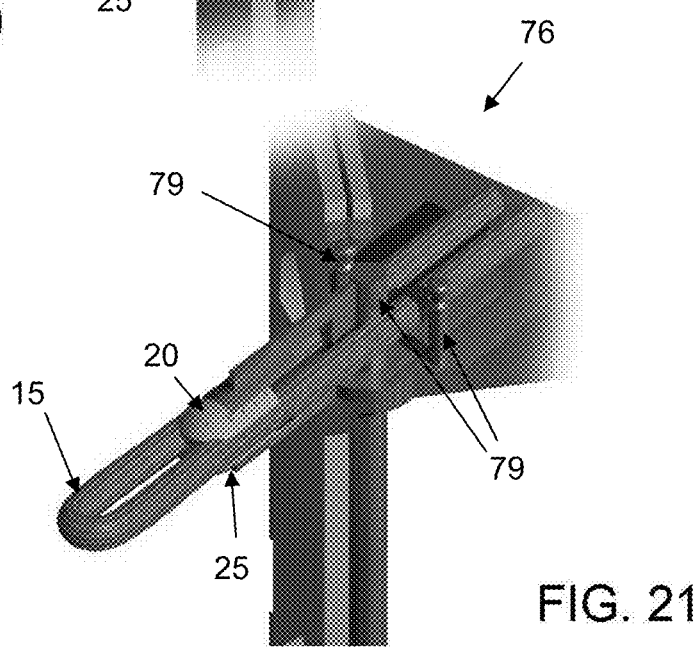
Figure 22:
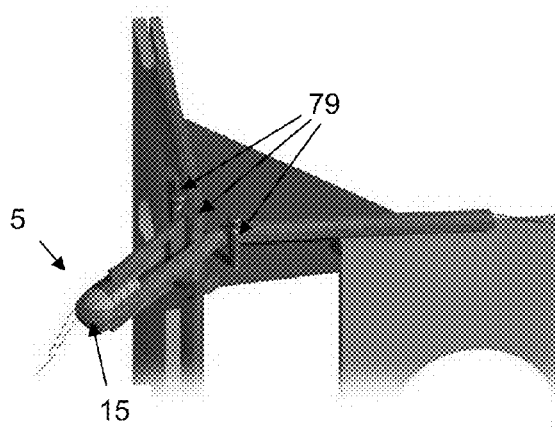
Figure 23:
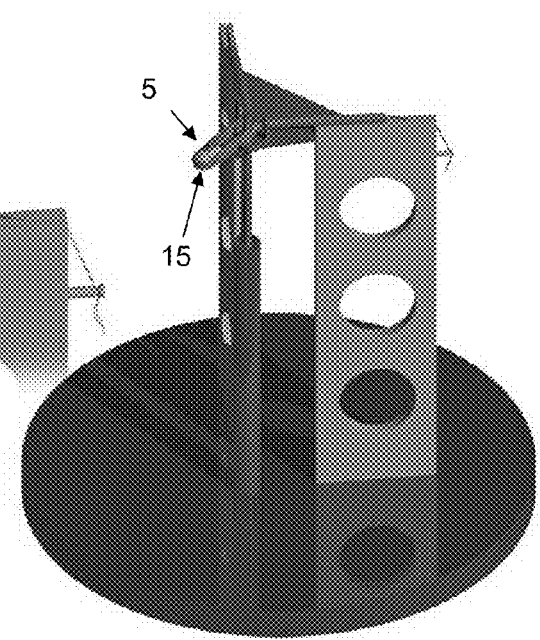

Thus, in this form of the invention, and looking now at FIGS. 10-12, after graft ligament 15 has been secured to plug 5 in the foregoing manner, and plug 5 has been secured to the distal end of inserter 40, inserter 40 and/or tow sutures 55 are used to advance plug 5 and its associated graft ligament 15 up into a bone tunnel, where it may be secured in place using an interference screw 60 (e.g., an interference screw of the sort sold by Arthrex). In this respect it will be appreciated that inasmuch as graft ligament 15 protrudes out of groove 10, the graft ligament will directly engage the side and end walls of the bone tunnel in order to facilitate successful osseointegration.

Where an interference screw is used to secure plug 5 in the bone tunnel, plug 5 may be provided with a shallow recess 65 in one of its exterior surfaces for receiving the interference screw. Preferably, recess 65 extends parallel to groove 10, but is set at a ninety degree angle to the groove (and the graft ligament protruding therefrom), so that interference screw 60 drives plug 5, but not graft ligament 15, against the opposing side wall of the bone tunnel. Thus, the engagement of graft ligament 15 with the side wall of the bone tunnel is not affected by the interference fit established by the interference screw. This can be significant, since it alleviates concerns about graft necrosis where an excessive interference force is created within the bone tunnel.

After interference screw 60 has been set so as to secure plug 5 against the opposing sidewall of the bone tunnel, inserter 40 may be disengaged from plug 5 and removed from the surgical site, leaving plug 5 supporting its associated graft ligament 15 within the bone tunnel.

FIGS. 13-15 show another form of the present invention. More particularly, the plug 5 shown in FIGS. 13-15 is substantially the same as the plug 5 shown in FIGS. 4-12, except that screws 70 are used to help secure first half 20 to second half 25. This can help ensure that the two halves do not become separated from one another after the graft ligament has been placed within groove 10, and can help compress the graft ligament between the two opposing halves.

FIGS. 16-19 show another form of the present invention. More particularly, the plug 5 shown in FIGS. 16-19 is substantially the same as the plug 5 shown in FIGS. 4-12, and/or the plug shown in FIGS. 13-15, except that first half 20 and second half 25 are connected together via a living hinge 75. This provision can facilitate mating of the two opposing halves.

FIGS. 20-23 show a fixture 76 which may be used to support first half 20 and second half 25 of plug 5 while graft ligament 15 is positioned within groove 10 and while first half 20 is mated to second half 25. To this end, fixture 76 preferably provides a pair of opposing supports 77, 78 for supporting first half 20 and second half 25, respectively. Fixture 76 may also include ligament management posts 79 for controlling the strands of graft ligament 15 while the graft ligament is secured to plug 5.

It should be appreciated that it is also possible to secure plug 5 (and its associated graft ligament 15) in a bone tunnel using means other than an interference screw.

Figure 24:
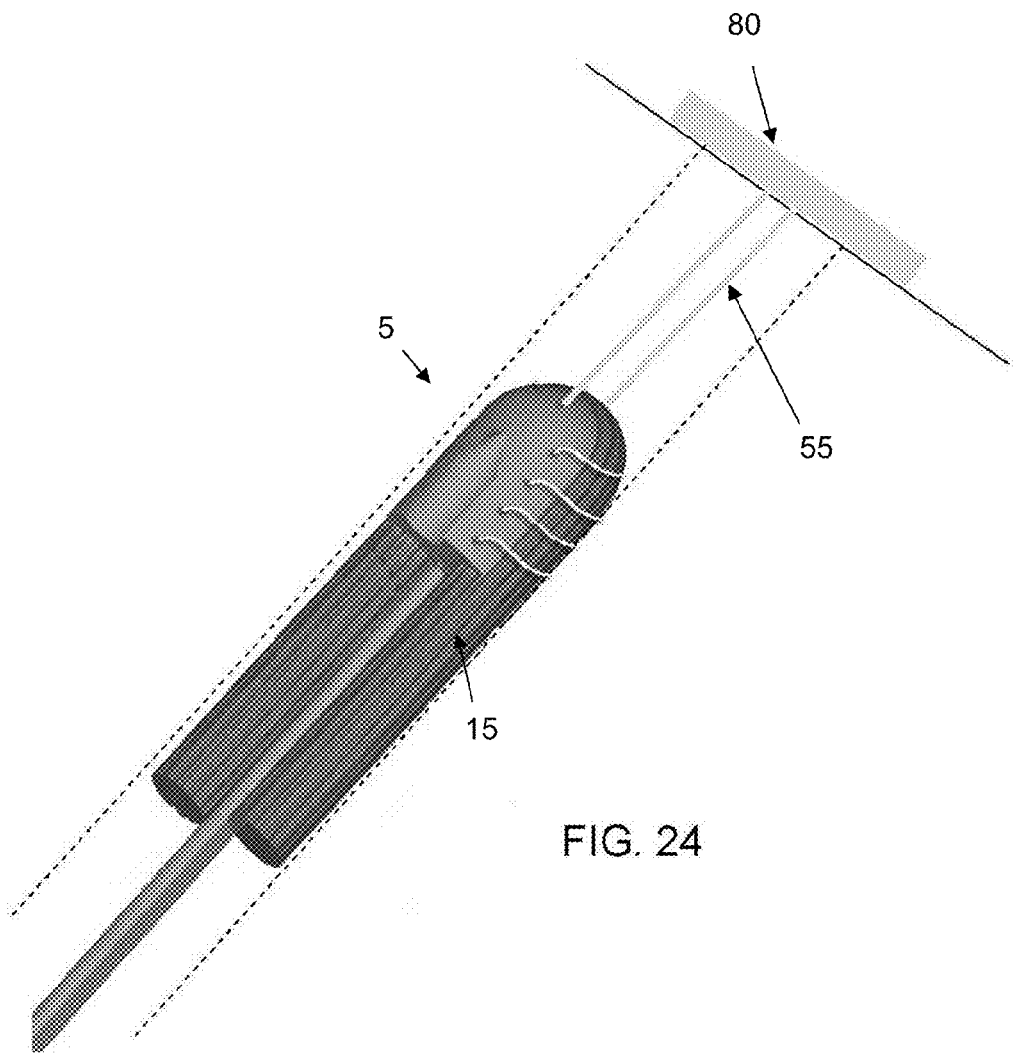
FIG. 24 is a schematic view showing the plug of FIGS. 4-12 secured in a bone tunnel with a suspension suture.

Thus, for example, and looking now at FIG. 24, tow sutures 55 may be used to suspend plug 5 within a bone tunnel. More particularly, after tow sutures 55 are used to position plug 5 (and its associated graft ligament 15) within the bone tunnel, the tow sutures may be stabilized utilizing a bearing or button structure 80 (e.g., an Endobutton™ of the sort sold by Smith & Nephew). Of course, where the femoral bone tunnel is formed as an open bore rather than as a blind hole, e.g., such as is shown in FIG. 24, there may be no end wall for the front loop of the graft ligament to engage. In this case, osseointegration occurs only along the side wall of the bone tunnel.

Figure 25:
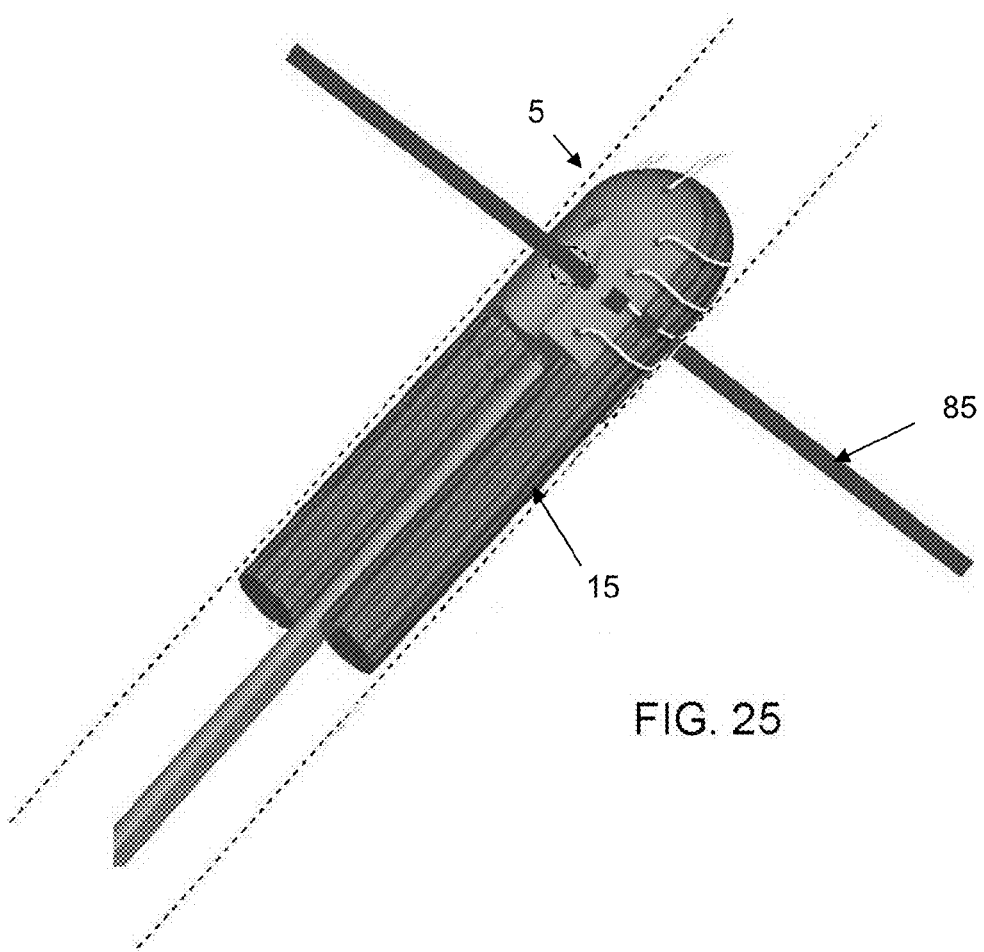
FIG. 25 is schematic view showing the plug of FIGS. 4-12 secured in a bone tunnel with a crosspin.

Alternatively, and/or additionally, and looking now at FIG. 25, plug 5 may be secured in a bone tunnel with a crosspin 85 (e.g., a crosspin of the sort sold by DePuy Mitek).

Some Aspects of the Invention

The plug is comprised of two mating halves that are brought together to form a single element.
The plug may be produced from bioresorbable polymer(s) or other materials (e.g., plastics, bovine bone, human bone, scaffolding material, etc.).
The assembled plug provides a recessed area to receive the graft ligament around the perimeter of the plug.
The plug halves may be connected to each other using screws or other connecting feature(s)/element(s).
The plug halves can be "loosely" joined together prior to wrapping the graft ligament, and then more tightly forced together after receipt of the graft ligament, introducing a clamping effect on the graft ligament.
The plug halves may incorporate gripping "teeth", stabbing protrusions, serrations, etc. that will provide increased means for securing the graft ligament to the plug.
The plug may incorporate a surface texture, a surface porosity, one or more blind holes, one or more surface slots, etc. so as to enhance osseointegration.
The plug may incorporate one or a plurality of bores and/or through-holes that facilitate blood flow through or along the plug, thereby enhancing osseointegration and/or resorption.
The plug may incorporate one or a plurality of holes around its perimeter, providing established locations for suturing the two plug halves together, with the graft ligament secured thereto, thereby producing a securely unitized "graft ligament plug".
The plug may incorporate holes at its distal end for introduction of towing suture to pull the assembled graft ligament plug into the femoral tunnel.
The plug may incorporate one or a plurality of recessed areas for receipt of an inserter (pushing/positioning tool) that can be used to insert the graft ligament plug into the femoral tunnel and/or to control plug rotation as it is advanced into the bone tunnel.
The plug may incorporate a recessed "starter area(s)" for accepting a(n) interference screw(s) to securely anchor the graft ligament plug in the femoral tunnel.
The plug can be one produced as a single element, requiring no joining of the halves.
The plug halves can be produced with a living hinge element and operate in a "clamshell" manner.
The plug halves can incorporate opposing ratcheting prongs and holes, allowing the two halves to be loosely joined to each other prior to receipt of the graft ligament and then firmly compressed together, introducing a locking and clamping effect on the graft.
The plug-graft assembly may be anchored in the femoral tunnel with a "crosspin" or "Endobutton-type" fixating device.
The system can include a "stand" or fixture to securely hold the plug in a desired orientation in space prior to insertion into the joint cavity—this stand frees the surgeon's hands from having to grip the plug while performing the operations of (i) joining the plug halves, (ii) wrapping the graft ligament around the plug, (iii) compressing the plug halves tightly onto the graft ligament, and (iv) suturing the two halves together with the graft ligament—this facilitates greater coordination/manipulation of the plug and graft elements, resulting in greater speed and ease in preparing a more secure assembly.
The system can include a pushing/positioning inserter tool to guide the plug to the correct position in the femoral tunnel—this tool may have retractable, scissor-action arms which, when inserted into a cavity formed in the plug, can extend outwardly and securely engage the plug, thereby allowing depth and rotational control of the plug prior to, and during, insertion of the interference screw.

One Preferred Method of Use

1. The two halves of the plug are brought together "loosely" (if not packed in a loosely joined configuration).

2. The graft ligament is wrapped around the loosely joined halves of the plug.

3. The two halves are firmly compressed together, forming a securely integrated assembly, with the graft protruding from the front (i.e., the distal end) and sides of the plug.

4. The plug and graft ligament may be sutured together, though it is not required, creating an important additional level of "binding" of the assembly into a permanently integrated whole.

5. The plug-graft assembly is securely affixed to the inserter.

6. The plug-graft assembly is advanced through tibial tunnel and up into the femoral tunnel using the inserter.

7. The plug-graft assembly is properly positioned in the femoral tunnel.

8. The interference screw is inserted, fixing the assembly in the femoral tunnel.

9. The inserter is retracted back through the tibial tunnel.

Optionally, tow sutures may be used to assist the inserter in advancing the plug-graft assembly up the tibial tunnel. And optionally, tow sutures may be used independent of an inserter in advancing the plug-graft assembly up the tibial tunnel. If desired, the inserter may be attached to the plug-graft assembly after it is located in the femoral tunnel so as to provide the surgeon with excellent rotational and depth control of the plug-graft assembly during final seating in the bone tunnel.

Some Advantages/Benefits of the Present Invention

The plug geometry allows for excellent graft ligament exposure and surface-to-surface contact between the graft ligament and the femoral tunnel wall (both side and end walls), promoting outstanding long-term biological connection between the graft ligament and the bone, resulting in excellent patient outcomes.

The plug "replicates" a bone-tendon-bone surgical ACL reconstruction procedure, thereby providing an excellent allograft or autograft alternative for those surgeons who are accustomed to and/or prefer the bone-tendon-bone surgical approach.

Use of the plug allows for fast, simple and secure ligament fixation without the introduction of complicated procedural steps or additional instrumentation.

The plug greatly improves a traditional ACL reconstruction procedure of simply fixing the graft ligament in the femoral tunnel with a large interference screw, by significantly enhancing the fixation with excellent graft exposure while removing any possibility of graft damage by direct contact with the interference screw.

Use of the inserter (pushing tool) provides the surgeon with excellent means to precisely locate the plug-graft assembly in the femoral tunnel while controlling rotation and depth during insertion of the interference screw.

MODIFICATIONS

It will be understood that many additional changes in the details, materials, steps and arrangements of parts, which have been herein described and illustrated in order to explain the nature of the invention, may be made by those skilled in the art while remaining within the principles and scope of the present invention.

What is claimed is:

1. An apparatus for use in supporting a graft ligament within a bone tunnel, the apparatus comprising:
    a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;
    wherein graft ligament plug is produced as a living hinge element connecting two halves, operating in a "clamshell" manner, such that the graft ligament can be positioned within the groove and thereafter clamped in said "clamshell" manner between the two halves of the graft ligament plug thereby completing the graft ligament plug.

2. An apparatus according to claim 1 further comprising an inserter/positioning tool with articulating fingers, releasably mounted to the plug, for advancing the graft ligament plug into the bone tunnel.

3. An apparatus according to claim 1 further comprising one or a plurality of holes providing established locations for suturing the two plug halves together and/or for introduction of towing suture for towing the graft ligament plug into the bone tunnel.

4. An apparatus according to claim 1 further comprising an interference screw for securing the graft ligament plug within the bone tunnel.

5. An apparatus according to claim 1 further comprising gripping "teeth", stabbing protrusions, and/or serrations, that will provide increased means for securing the graft ligament to the plug.

6. An apparatus according to claim 1 wherein a recessed "starter area(s)" for accepting an interference screw(s) to securely anchor the graft ligament plug in the femoral tunnel.

7. An apparatus according to claim 1 wherein the plug may incorporate a surface texture, a surface porosity, one or more blind holes, one or more surface slots, etc. so as to enhance osseointegration and/or resorption.

8. An apparatus according to claim 1 wherein the plug halves incorporate opposing ratcheting prongs and holes, allowing the two halves to be loosely joined to each other prior to receipt of the graft ligament and then firmly compressed together, introducing, under well-controlled compression (ratcheting), a mating and locking of the halves and a locking and clamping effect on the graft, so as to form the complete graft ligament plug.

9. An apparatus for use in supporting a graft ligament within a bone tunnel, the apparatus comprising:
    a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;
    wherein the graft ligament plug is formed in two opposing halves, such that the graft ligament can be positioned within the groove and thereafter clamped between the opposing two halves of the graft ligament plug when the two opposing halves are brought together so as to form the complete graft ligament plug, and wherein a crosspin is used for supporting the graft ligament plug within the bone tunnel.

10. An apparatus according to claim 9 further comprising an interference screw for securing the graft ligament plug within the bone tunnel.

11. An apparatus according to claim 9 further comprising one or a plurality of holes providing established locations for suturing the two plug halves together and/or for introduction of towing suture for towing the graft ligament plug into the bone tunnel.

12. An apparatus according to claim 9 wherein the plug halves incorporate opposing ratcheting prongs and holes, allowing the two halves to be loosely joined to each other prior to receipt of the graft ligament and then firmly compressed together, introducing, under well-controlled compression (ratcheting), a mating and locking of the halves and a locking and clamping effect on the graft, so as to form the complete graft ligament plug.

13. A method for supporting a graft ligament within a bone tunnel, the method comprising:
    providing a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;
    wherein the graft ligament plug is formed in two opposing halves, such that the graft ligament can be positioned within the groove and thereafter clamped between the opposing two halves when the halves are brought together so as to form the complete graft ligament plug;
    mounting a graft ligament to the graft ligament plug so that the graft ligament protrudes from the groove of the graft ligament plug;
    positioning the graft ligament plug and the graft ligament within the bone tunnel; and supporting the graft ligament plug within the bone tunnel using a crosspin.

14. A method according to claim 13 wherein an interference screw is used for securing the graft ligament plug within the bone tunnel.

15. A method according to claim 13 wherein the plug and graft ligament may be sutured together, creating a permanently integrated whole.

16. A method according to claim 13 wherein the plug halves, which incorporate opposing ratcheting prongs and holes, are loosely joined to each other prior to receipt of the graft ligament and then firmly compressed together, introducing, under well-controlled compression (ratcheting), a mating and locking of the halves and a locking and clamping effect on the graft, so as to form the complete graft ligament plug.

17. A method for supporting a graft ligament within a bone tunnel, the method comprising:
    providing a graft ligament plug, the graft ligament plug comprising a groove extending along one side of the plug, across the front end of the plug, and then back down the opposing side of the plug, with the groove being sized such that when a graft ligament is disposed in the groove, the graft ligament will protrude out of the groove and engage adjoining portions of the bone tunnel so as to facilitate osseointegration therewith;
    wherein graft ligament plug is produced as a living hinge element connecting two halves, operating in a "clamshell" manner, such that the graft ligament can be positioned within the groove and thereafter clamped in said "clamshell" manner between the two halves of the graft ligament plug thereby completing the graft ligament plug;
    mounting a graft ligament to the graft ligament plug so that the graft ligament protrudes from the groove of the graft ligament plug;
    positioning the graft ligament plug and the graft ligament within the bone tunnel; and supporting the graft ligament plug within the bone tunnel.

18. A method according to claim 17 wherein an interference screw is used for securing the graft ligament plug within the bone tunnel.

19. A method according to claim 17 wherein the plug and graft ligament may be sutured together, creating a permanently integrated whole.

20. A method according to claim 17 wherein the plug halves, which incorporate opposing ratcheting prongs and holes, are loosely joined to each other prior to receipt of the graft ligament and then firmly compressed together, introducing, under well-controlled compression (ratcheting), a mating and locking of the halves and a locking and clamping effect on the graft, so as to form the complete graft ligament plug.

* * * * *